United States Patent [19]

Erskine

[11] Patent Number: 5,141,497

[45] Date of Patent: Aug. 25, 1992

[54] APPARATUS AND METHOD FOR AN INTRODUCER

[75] Inventor: Timothy J. Erskine, Salt Lake City, Utah

[73] Assignee: Becton, Dickinson and Company, Franklin Lakes, N.J.

[21] Appl. No.: 362,136

[22] Filed: Jun. 6, 1989

[51] Int. Cl.⁵ ............................................. A61M 5/178
[52] U.S. Cl. ..................................... 604/165; 604/160; 604/177
[58] Field of Search .............................. 604/164–170, 604/177, 178, 264, 280, 283, 160

[56] References Cited

U.S. PATENT DOCUMENTS

| | | | |
|---|---|---|---|
| 3,537,451 | 11/1970 | Murray et al. | 604/165 |
| 4,192,305 | 3/1980 | Seberg | 604/165 |
| 4,311,137 | 1/1982 | Gerard | 604/167 X |
| 4,362,156 | 12/1982 | Feller, Jr. et al. | 604/165 |
| 4,392,856 | 7/1983 | Lichtenstein | 604/177 |
| 4,411,654 | 10/1983 | Boarini et al. | 604/165 |
| 4,412,832 | 11/1983 | Kling et al. | 604/164 |
| 4,471,778 | 9/1984 | Toye | 604/166 X |
| 4,581,019 | 4/1986 | Curelaru et al. | 604/164 |
| 4,581,025 | 4/1986 | Timmermans | 604/264 |
| 4,772,266 | 9/1988 | Groslong | 604/164 |
| 4,776,846 | 10/1988 | Wells | 604/161 |
| 4,865,593 | 9/1989 | Ogawa et al. | 604/264 |

Primary Examiner—John D. Yasko
Assistant Examiner—Adam J. Cermak
Attorney, Agent, or Firm—Arthur D. Dawson

[57] ABSTRACT

The introducer has an adapter with a pair of wings extending at an acute angle to each other wherein the wings are used in handling, holding and splitting. A splittable catheter mounts in a part of the adapter and extends in alignment with an axis of the adapter. The adapter is molded about the splittable catheter tube. A needle and hub are in axial alignment with one another so the needle fits within the splittable catheter coaxial with the axis and the hub removably locks to the adapter to hold the splittable catheter coaxially about the needle during insertion of the needle and splittable catheter with an over the needle technique. Interengagement means on the adapter and the hub lock the axial relationship of the needle within the splittable catheter. An apex between the acute of the wings is parallel to the passageway therethrough and a weakened line is on a side of the adapter opposite the apex so that force applied to the wings to reduce the acute angle thereof will separate the weakened line and the apex initiating tearing of the splittable catheter. The method for using and making an introducer includes the steps of holding a winged adapter with the fingers of one hand, inserting the needle and splittable catheter into a blood vessel, releasing the lock between the adapter and the hub, removing the hub by withdrawing the needle from the catheter and squeezing the wings together to split the adapter and the catheter.

19 Claims, 5 Drawing Sheets

APPARATUS AND METHOD FOR AN INTRODUCER

BACKGROUND OF THE INVENTION

1. Field of the Invention

This invention relates to an apparatus and method for introducing a splittable catheter and thereafter splitting the catheter with a winged adapter. More particularly, the introducer herein is for one handed introduction of a splittable catheter and thereafter initiating the splitting of the catheter with the one hand pressing the wings of the adapter together.

2. Background Description

The invention described in this application is related to the subject matter in U.S. application Ser. No. 838,739 filed Mar. 11, 1986, now U.S. Pat. No. 4,661,300, issued Apr. 28, 1987 and co-pending U.S. application Ser. No. 011,783 filed Feb. 6, 1987 now U.S. Pat. No. 4,776,846 and co-pending U.S. application Ser. No. 227,040, filed Aug. 1, 1988, now U.S. Pat. No. 4,952,359, and U.S. application Ser. No. 191,523, filed May 9, 1988, now abandoned.

Splittable introducer catheters are used in inserting long-term catheter arrangements into patients. That is, when attempting to insert long-line catheters into the human body the procedure includes making the venipuncture with a hollow needle that carries coaxially thereover a splittable placement or introducer catheter of the kind to which this invention is directed. Once the vein has been penetrated, and blood is visible in the flashback chamber of such an assembly, the needle and flashback chamber are removed leaving the placement catheter through the site of the puncture and into the lumen of the vessel.

Thereafter, a long-line catheter or guidewire is threaded through the placed catheter, and thereafter the catheter is removed from the vein by axial sliding movement along the guidewire, for example, leaving the guidewire or long-line catheter in place. The removed placement or introducer catheter is designed to split longitudinally from its coaxial position over the guidewire or long-line catheter, so that it may be readily removed without any difficulty or irritation to the patient.

With respect to the above-noted U.S. Pat. No. 4,776,846 that patent teaches an invention for producing a splittable introducer or placement catheter with diametrically opposed longitudinally extending grooves positioned in the outer surface of the placement catheter. These grooves facilitate the stripping of the introducer catheter once the guidewire and long-line catheter are in place. A difficult part of handling catheters of the kind discussed herein is the entry when carried over a needle and through the skin of a patient and any trauma or other undesirable circumstances caused thereby. Specifically the placement of the splittable catheter in the vessel requires skill, technique and an easily controlled introducer.

U.S. Pat. No. 4,377,165 shows a needle with longitudinal fracture lines that is split by pulling apart a pair of finger-wings with two hands. The use of a splittable needle to introduce a catheter or guide wire is not favored because the rigid needle tends to irritate the lining of the vessel lumen. A non-rigid introducer reduces the risk of tissue damage and/or damage to the indwelling device as it is inserted and adjusted, and prevents patient injury or death from a catheter severed by a rigid introducer. U.S. Pat. No. Re. 31,855 shows a splittable catheter of linearly oriented material that tears readily in the longitudinal direction propagated by pulling tabs attached to opposite sides of the catheter. U.S. Pat. No. 4,581,025 shows several different embodiments of the preceding reissue patent. U.S. Pat. No. 4,412,832 has a peelable catheter with score lines and a sliding suture sleeve to prevent premature splitting. U.S. Pat. No. 4,411,654 has an anti-rotation feature and finger-loops to peel catheter. Braun, a West German company, markets a product with a splittable catheter having a longitudinally tearing tube initiated by pulling apart two tabs which break the catheter adapter in half.

The adapter for the splittable catheter has to include something to tear the splittable catheter apart and still be easy to handle during the insertion procedure. A single handed introduction is preferred because the other hand is free to hold the patient's arm, for example. Therefore an adapter which has a needle that is held within the catheter is preferred. U.S. Pat. No. 4,362,156 shows opposing latches attached to a needle hub which lock onto a catheter adapter. U.S. Pat. No. 4,192,305 shows a pawl type latch holding a catheter to a needle hub.

SUMMARY OF THE INVENTION

An introducer comprises an adapter with a first end and a second end and a first part on the first end and a second part on the second end. The adapter has a passageway aligned along an axis of the adapter and passing therethrough. The adapter also has a pair of wings extending outwardly from the adapter with an acute angle between the wings for use in handling, holding and splitting the adapter. The adapter may include an apex along the place where the wings attach to the adapter and parallel to the passageway and near the second part.

A splittable catheter mounts in the first part of the adapter and extends outwardly from the first end in alignment with the axis of the passageway and in fluid tight communication therewith. A needle and hub means has a needle and a hub in axial alignment with one another so the needle fits within the splittable catheter coaxial with the axis and the hub removably locks to the adapter to hold the splittable catheter coaxially about the needle during insertion of the needle and splittable catheter with an over the needle technique.

Interengagement means on the adapter and the hub cooperatively locks the axial relationship of the needle within the splittable catheter upon placement of the needle within the splittable catheter so that the hub is against the second end of the adapter. The interengagement means has an unlocking member for release of the lock of the adapter to the hub. The unlocking member extends from the hub and is movable relative thereto in response to engagement of a portion thereof with the second part upon conjugation of the needle within the splittable catheter tube. The unlocking member has a latch to connect with the second part when the hub is against the second end. The second part has a catch between the wings; the wings have opposed facing surfaces including ribs extending from the apex toward each other in planes normal to facing surfaces of the wings. The latch is movable from a position of engagement to a position of unlocking and upon coaxial positioning of the needle in the splittable catheter the latch automatically engages the catch.

The needle, including a beveled tip, fits in sliding relation within the splittable catheter with the tip of the needle extending beyond the splittable catheter for penetration into a lumen of a vessel upon insertion of the splittable catheter and needle. The needle is movable axially through the splittable catheter and the passageway during removal of the needle from the splittable catheter after insertion with an over the needle procedure and after unlocking of the interengagement means.

A weakened line is on a side of the adapter opposite the apex so that force applied to the wings to reduce the acute angle therebetween will separate the weakened line and then the apex initiating tearing of the splittable catheter near the first end. The adapter receives and mounts in the first part the splittable catheter extending outwardly from the first end in alignment with the axis of the passageway and in fluid communication therewith. The first part includes an expandable attachment so that the splittable catheter tears upon splitting of the first part. Force applied to the wings to collapse the acute angle breaks the adapter along a side opposite the apex and then continued collapse of the acute angle of the wings separates the adapter along the apex. As an alternative pair of weakened lines are along the adapter with one at the apex and the other on the opposite side to encourage breaking of the adapter along the lines upon application of stress to the wings. A fulcrum means on the wings meets during the collapse of the wings and transfer the stresses applied to collapse the wing to the apex.

The adapter may preferably be molded about the splittable catheter to form the fluid tight communication between the adapter passageway and the splittable catheter tube. The adapter is made of an inflexible filled polymeric substance and the hub is made of a polymeric substance which is more flexible than the polymeric substance of the adapter. The adapter and hub are molded of polymeric substances which are compatible with one another for attachment to one another.

The method for using and making an introducer includes the steps of holding an introducer with the fingers of one hand, the introducer having a winged adapter with a splittable catheter and a needle and hub in axial alignment with one another and locked to the catheter and inserting the needle and splittable catheter with an over the needle technique into a blood vessel. The added steps of releasing the lock between the winged adapter and the needle and hub with the finger of the one hand, removing the needle and hub means by withdrawing the needle and hub from the splittable catheter and adapter with the one hand and squeezing the wings of the adapter together to cause the adapter and the catheter to split.

The method may include the additional steps of introducing a catheter through the splittable catheter prior to the squeezing step and attaching the splittable catheter and winged adapter by molding the winged adapter about the splittable catheter at an end thereof during the manufacture thereof.

DETAIL DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiments illustrated. The scope of the invention will be measured by the appended claims and their equivalents.

The introducer 10 has a winged adapter 11 and a hub and needle 12; the winged adapter 11 can initiate and propagate the separation of a splittable catheter or tube 13 with the pinching action of two fingers or a thumb and a finger as shown in FIGS. 1 through 4. A latch or an interengagement means 24 for mechanically fastening the needle and hub 12 to the winged adapter 11, such that the needle and hub 12 is locked and then easily detached and removed once the splittable catheter 13 and winged adapter 11 has been successfully placed in the body at A in FIGS. 1, 2 and 3. The splittable catheter 13 and winged adapter 11 and interlocking needle and hub 12 are used in an over the needle insertion procedure.

The winged adapter 11 has a first end 14 and a second end 15 and there is a first part 16 on the first end 14 and a second part 17 on the second end 15. The adapter has a passageway 18 aligned along an axis B of the winged adapter 11 and passing therethrough from the first end 14 to the second end 15. The winged adapter 11 also has a pair of wings 19 and 20 extending outwardly from the winged adapter 11 at an acute angle C for use in handling, holding and splitting the winged adapter 11. The winged adapter includes an apex 21 along the place where the wings 19 and 20 attach to the winged adapter 11 so that the apex 21 is parallel to passageway 18 and near the second part 17.

Figure 3:
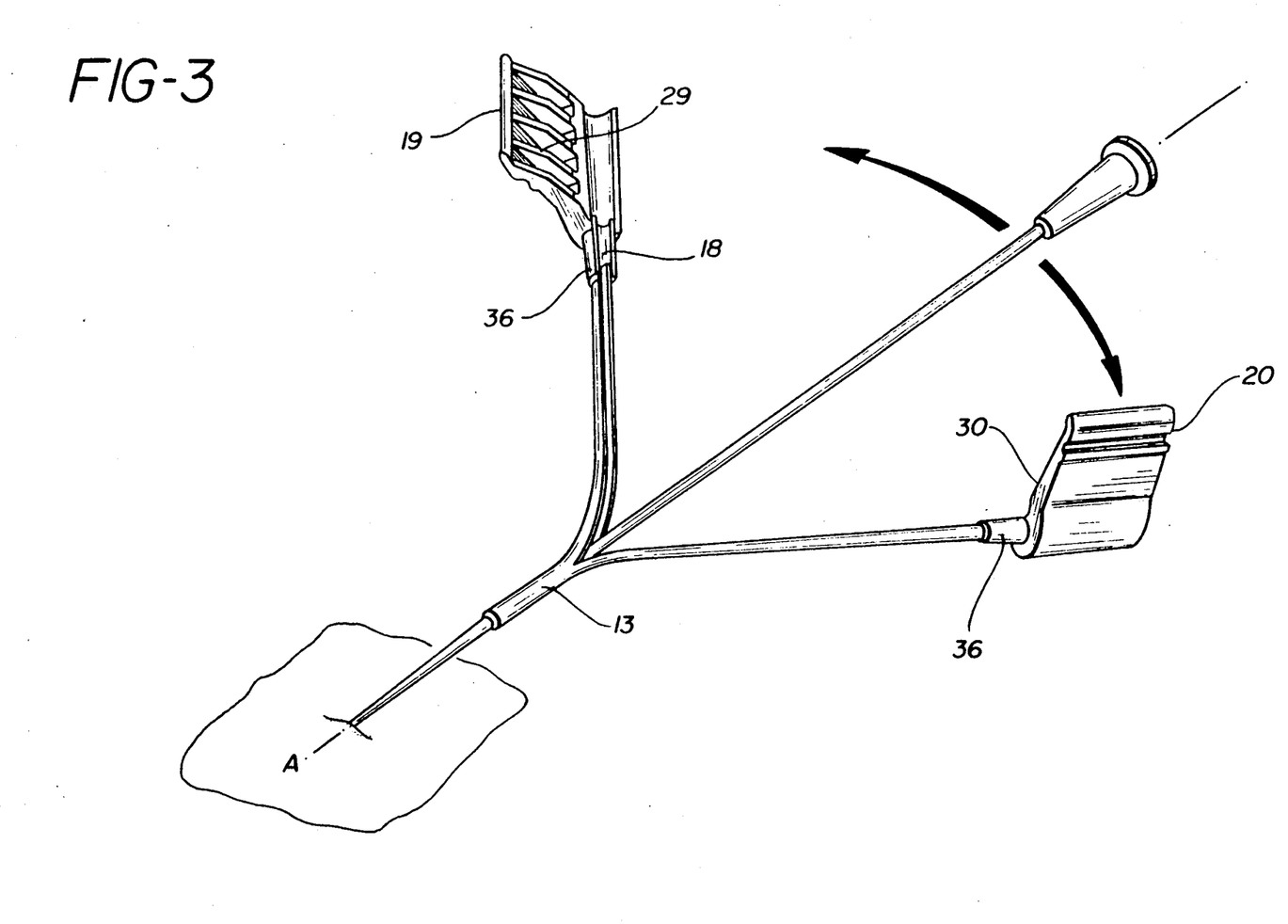
FIG. 3 is an illustration of the adapter of FIGS. 1 and 2 wherein the needle and hub have been removed from the adapter and splittable catheter which has been split after a long catheter was inserted therethrough and into the patient.
Figure 5:
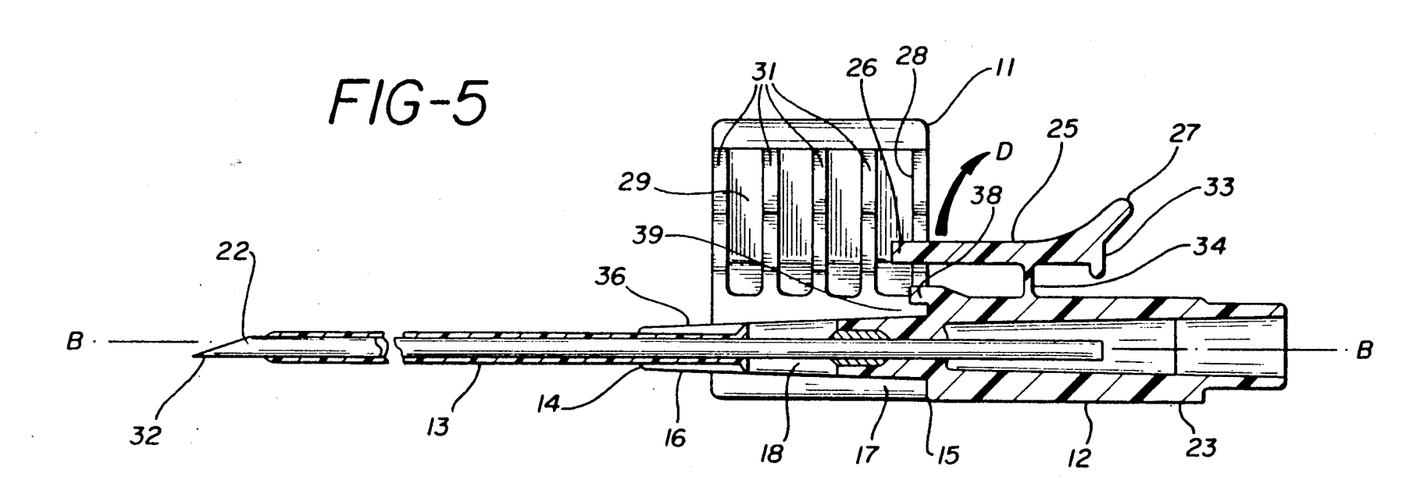
FIG. 5 is a side cross-sectional along line 5—5 of FIG. 1 of the introducer having an adapter for a splittable catheter and a hub and needle locked thereto.
Figure 6:
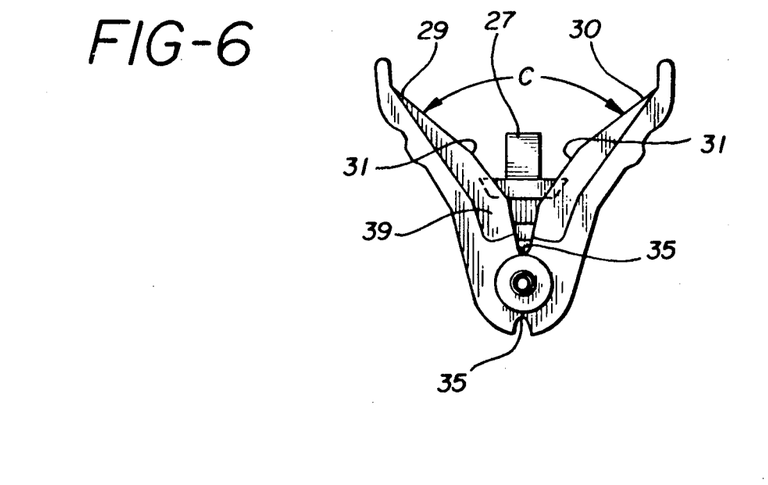
FIG. 6 is an end view taken along line 6—6 in FIG. 1 of the adapter and hub locked thereto.

The splittable catheter 13 mounts within the first part 16 of the winged adapter 11 and extends outwardly from the first end 14 in alignment with the axis B of the passageway 18, see FIGS. 3 and 5 so as to be in fluid tight communication therewith. The needle and hub 12 includes a needle 22 being a hollow elongate metallic thin wall tubular member and a molded polymeric hub 23 fastened to the needle 22 so that it fits within the splittable catheter 13 in coaxial position relative to the axis B and the passageway 18 of the winged adapter 11. The hub 23 removably locks to the winged adapter 11 to hold the splittable catheter 13 coaxially about the needle 22 during an over the needle insertion procedure of the splittable catheter 13.

Figure 1:
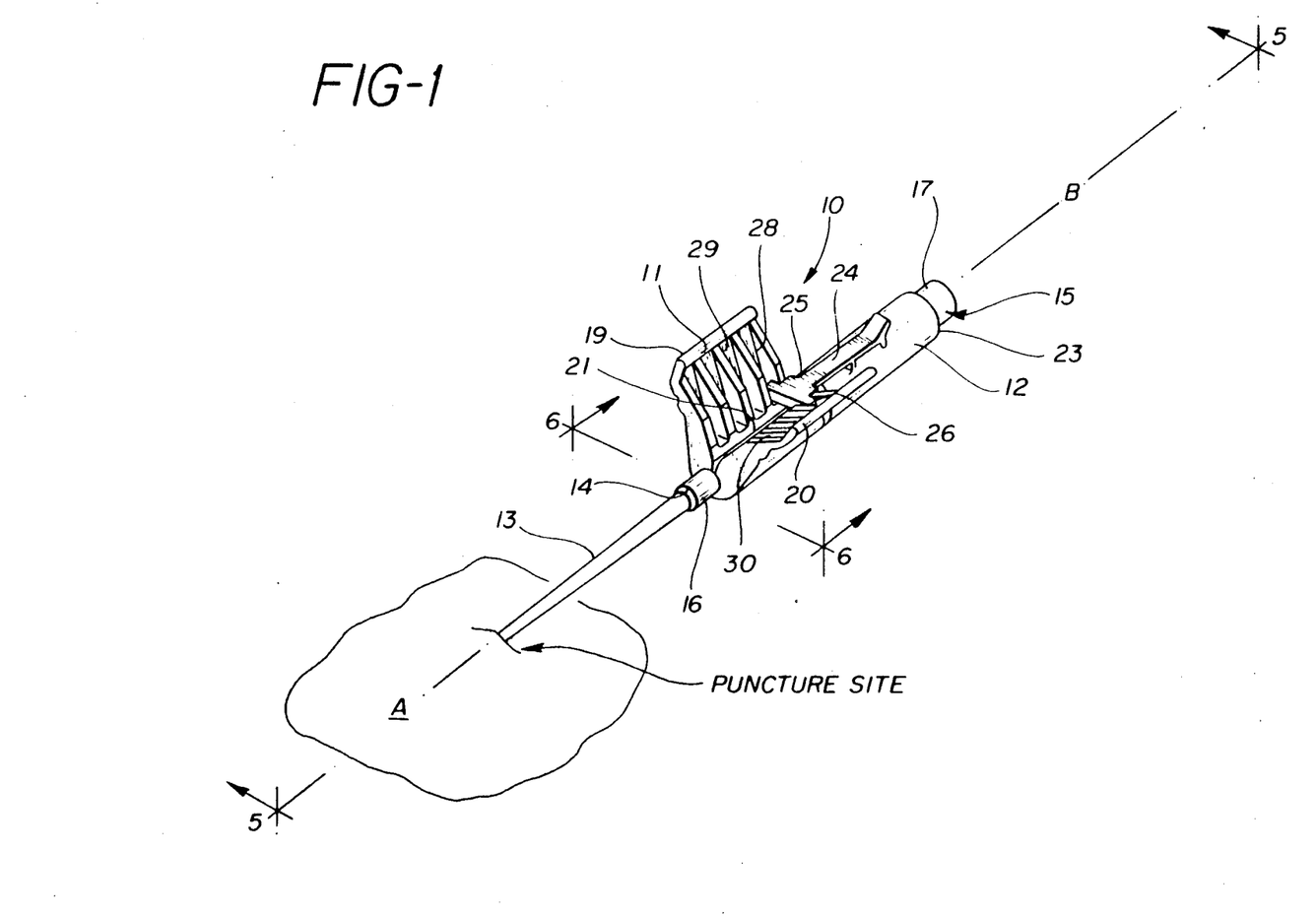
FIG. 1 is a perspective view of the preferred embodiment of an introducer having an adapter for a splittable catheter and a hub and needle locked thereto shown with the introducer inserted into a puncture site.
Figure 2:
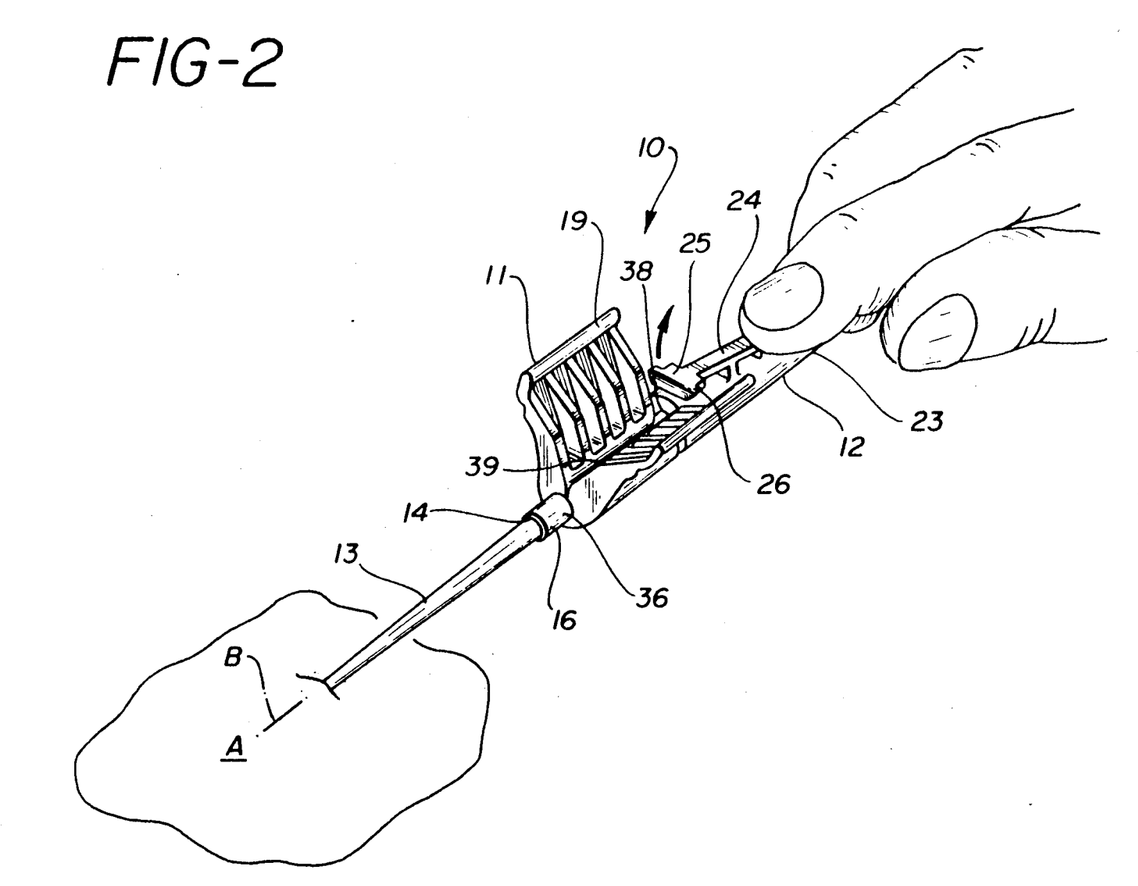
FIG. 2 is a perspective view of the preferred embodiment of an introducer having an adapter for a splittable catheter and a hub and needle locked thereto with the medical practitioner's finger pressing against a releasable latch to unlock the hub from the adapter.

Introducer 10 has an interengagement means 24, best shown in FIGS. 1, 2 and 5, on the winged adapter 11 and the hub 23 so as to cooperatively lock the axially relationship of the needle 22 within the splittable catheter 13 during placement of the needle into a vessel lumen. The interengagement means 24 holds the hub 23 against the second end 15 of the winged adapter 11. The interengagement means 24 has an unlocking member 25 for release of the locking engagement of the winged adapter 11 and the hub 23.

The unlocking member 25 extends from the hub 23 and is movable relative thereto in response to engagement of a portion 26 thereof with the second part 17 upon axial conjugation of the needle 22 within the splittable catheter 13. The unlocking member 25 has a latch 26 in the form of a transverse part or T-bar configured to connect with the second part 17 when the hub 23 is against the second end 15. The second part 17 has a catch 28 located between the wings 19 and 20. The wings 19 and 20 have opposed facing surfaces 29 and 30, respectively. The wings 19 and 20 include ribs 31 which extend from the apex 21 toward each other in planes normal to the opposed facing surfaces 29 and 30 of the wings 19 and 20.

The latch 27 is movable from a position of nonengagement with the ribs 31 to a position of locking with the winged adapter 11 upon full insertion of the needle 22 into the splittable catheter 13. With application of finger pressure as shown in FIG. 2 the latch 27 is moved to disengage from the ribs 31 as in FIG. 2. In particular, portion 26 of the locking member 25 is cammed over the ribs 31 as the hub 23 seats against the second end 15. The latch 27 may only be released manually but engagement is automatic upon placement of the hub 23 against the second end 15 of the winged adapter 11.

The needle 22 has a beveled tip 32 which fits in sliding relation within the splittable catheter 13 so that the tip 32 of the needle 22 extends beyond the splittable catheter 13 in position for penetration into a lumen of a vessel when inserting the splittable catheter 13 and needle 22. The needle 22 is axially movable through the splittable catheter 13 and the passageway 18 of the winged adapter 11 for removal of the needle 22 from the splittable catheter 13 after insertion with an over the needle procedure and after unlocking the interengagement means 24. This is done by pressing on the latch 27 as shown in FIG. 2 to rotate the latch 27 unlocking member 25 in a clockwise direction as illustrated by arrow D in FIG. 5 thus causing the latch 27 to lift the portion 26 from the ribs 31.

A nib 33 is provided on the latch 27 to prevent movement of the latch 27 in an arc D in FIG. 5 as shown by arrow D beyond the distance which would stretch a hinge 34 past its elastic limit. The hub 23 is molded of a relatively flexible polyurethane material whereas the winged adapter 11 is preferably molded of a similar polyurethane which has added to it a filler such as barium sulfate. The filler is added in order to make the winged adapter 11 more brittle for purposes of fracture during splitting as will be explained. The preferred amount of barium sulfate is approximately 30% by weight.

A weakened line 35 on the side of the winged adapter 11 opposite the apex 21 defines the first of failure when the wings 19 and 20 are stress. The weakened line 35 fractures, breaks or separates along the weakened line 35. In particular, the acute angle C of the winged adapter 11 is reduced when force is applied to the wings 19 and 20 as shown in the three illustrative views of FIG. 4. Separation of the winged adapter 11 causes the splittable catheter 13 to tear near the connection thereof with the winged adapter 11 near first end 14. An expandable attachment 36 is provided on the first part 16 by molding the winged adapter 11 about the end of the splittable catheter 13 during manufacture.

Figure 4:
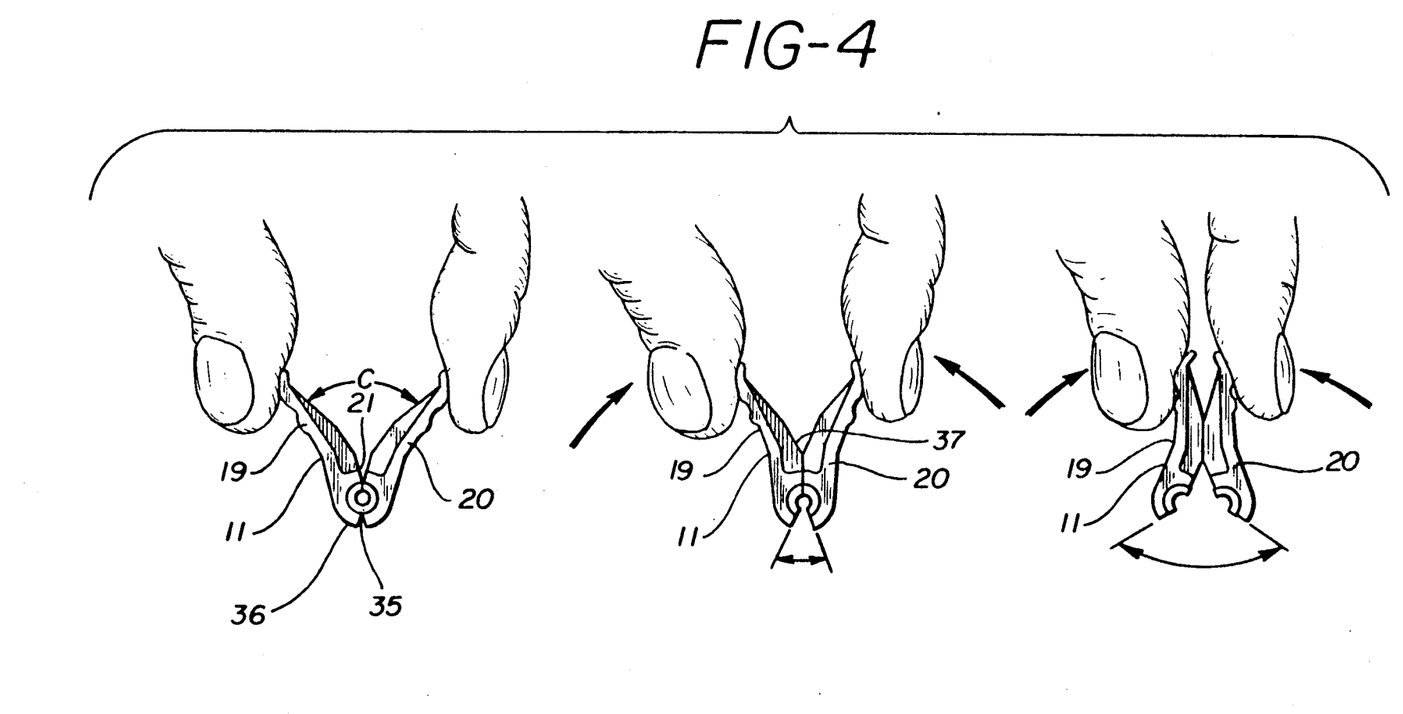
FIG. 4 is a series of three illustrations of the adapter of FIGS. 1 and 2 wherein the catheter is not shown although the adapter is depicted from the end from which the catheter would extend and the three illustrations show how the adapter splits under pressure applied to the wings thereof by the medical practitioner's thumb and index finger.

As explained, forces applied to the wings 19 and 20 to collapse the acute angle C break the winged adapter 11 along the side opposite the apex 21 and then continued the collapse of the acute angle C of the wing separates the adapter along, the apex 21 as shown in the last view of FIG. 4. As an alternative arrangement a pair of weakening lines 35 may be used along the adapter with one at the apex 21 and the other on the opposite side of the winged adapter 11 to encourage breaking of the adapter, first along weakened line 35 on the side opposite and then upon the apex 21. A fulcrum means 37 is cooperatively associated with the wings 19 and 20 and resides on a portion of ribs 31 such that during the collapse of the wings 19 and 20 the stress applied to collapse the wings is brought to bear on the meeting fulcrum means 37 which touch and are the first points of contact of the wings so as to apply a lever load along the apex 21 as illustrated in the middle view of FIG. 4.

The method for using and making the introducer 10 includes the steps of holding the introducer 10 with the fingers of one hand, the introducer 10 has a winged adapter 11 with a splittable catheter 13 and a needle and hub 12 in axially alignment with one another and locked to each other. Thereafter the method includes the steps of inserting the needle 22 and splittable catheter 13 with an over the needle technique into a blood vessel and releasing the lock between the winged adapter 11 and the needle and hub 12 with a finger of the hand. Following that the steps, of removing the needle and hub 12 by withdrawing them from the winged adapter 11 and splittable catheter 13 with the one hand while squeezing the wings of the winged adapter 11 together to cause it and the splittable catheter 13 to separate into two halves are used.

Typical use of the splittable introducer 10 for placement of a central venous access catheter is as follows:

a.) Insertion of the introducer-catheter is made into a prepared patient puncture site and proper placement is verified by blood flashback and/or aspiration.

b). The needle/interlocking hub subassembly is detached and withdrawn from the introducer-catheter and discarded.

c). A central venous access catheter is threaded through the introducer-catheter and into the vessel.

d). The introducer-catheter is partially withdrawn from the puncture site and the adapter is split with finger pressure.

e). The two halves of the adapter are pulled apart, separating the splittable catheter tubing while withdrawing it from the puncture site. The introducer-catheter is discarded.

f). The central venous access catheter is positioned and secured.

The splitting of the winged adapter 11 is initiated by squeezing the pair of molded adapter wings 19 and 20 protruding from the winged adapter 11 at acute angle C and the length of the wings 19 and 20 is such that they can be grasped between the thumb and forefinger of one hand. The winged adapter 11 has two longitudinal lines 35 of reduced wall thickness, diametrically opposed and aligned between the wings 19 and 20 such that compressive finger pressure will successively induce tensile failure in each of the lines 35. The splitting sequence is as follows:

a). Initial finger pressure, acting through the lines 35 between the wings, separates the lines 35 opposite the wings.

b). The wings 19 and 20 pivot toward each other about the apex 21 between them until contact is made on the stiffening ribs 31 situated on the inside of each wing.

c). Continued finger pressure, acting through the contact point on the ribs 31, fails the apex 21 between the wings and separates the winged adapter 11 into two halves.

The splittable catheter 13 is attached by molding the winged adapter 11 thereto, such that the two diametrically opposed lines of weakness 35 on the catheter 13 coincide with the fracture plane of the winged adapter 11. Upon splitting, the first part of the winged adapter 11 is bisected and each half of the winged adapter 11 works in an outward and opposite manner upon the splittable catheter 13 initiating separation along the lines of weakness. Each half of the splittable catheter 13 remains attached to a half of the split adapter 11, facilitating complete separation of the splittable catheter 13.

The interengagement means 24 for connecting the needle hub 23 to the winged adapter 11 has a latch 27 integral to the needle hub 23. The latch 27 extends parallel to the longitudinal centerline or axis B of the adapter 11, and connects to the hub 23 by means of unlocking member 25 such that rocking the latch 27 to release the winged adapter 11 does not stress the hinge 34 beyond its yield point. The nib 33 prevents over stress of the hinge 34 by limiting rotation of the member 25. The latch 27 engages the splittable adapter by means of portion 26 or transverse part or T-bar on the forward end of the latch which T-bar bridges between the aftmost pair of stiffening ribs on the splittable adapter. Attempted separation of the hub 23 and adapter 11 is prevented by the engagement of the ribs 31 against the ends of the T-bar, which prevents separation as in FIG. 1.

To detach the hub 23 from the adapter 11, finger pressure exerted on the aft-end of the latch 27, causes the T-bar to move away from the adapter 11. With the T-bar in this position FIG. 2, the distance between the ribs of the adapter 11 is greater than the width of the T-bar, and the hub 23 may be withdrawn from the adapter 11 without interference. A key 38, protruding from the needle hub 23 beneath the T-bar, fits into a groove 39 between the wings 19 and 20 to ensure correct angular orientation of the hub 23 with the adapter 11, and to prevent excessive torsion of the latch 27 about the member 26.

Those skilled in the art will appreciate that the introducer is the first splittable type introducer which offers the advantages of insertion technique identical to conventional intravenous over the needle catheters and can be initially split using only one hand. It has a positive lock between the needle hub and catheter adapter with a simple means of disengagement. The catheter attachment ensures adequate outward tube splitting force and a hermetic seal. Suitable alternatives for the splittable adapter include any variation in the method of splittable tubing attachment, width, length, and shape of wings and their geometry to facilitate a translating fulcrum, and material used for fabrication. Alternatives for hub include choice of material, T-bar and latch geometry, and method of causing radial T-bar motion with respect to the adapter body. The wings, the latch, the weakened line and the catch may take any geometric form so long as the hub and adapter are still capable of permitting the one hand operation. The specific material described and the particular configurations of the preferred embodiments may be changed without departing from the scope of the invention covered by the claims which follow.

What is claimed is:

1. An introducer comprising:

an adapter with a first end and a second end and a first part on the first end and a second par ton the second end, the adapter having a passageway aligned along an axis thereof and passing therethrough to the second end, the adapter having a pair of wings each having a tip and a mount on and extending from the adapter, the mounting of the wings arranged to initiate splitting o the adapter as the tips of the positioned wings are brought toward one another;

a splittable catheter mounted to the first part of the adapter and extending outward from the first end in alignment with the axis of the passageway and in fluid tight communication therewith, the adapter weakened on a line substantially parallel its axis and the pair of wings positioned on the adapter so that an apex parallel to the axis is formed by the planes of the wings, which are positioned at an angle about 90° or less relative to one another and substantially 180° away from the weakened line;

a needle and hub means having a needle and a hub i axial alignment with one another so the needle fits within the splittable catheter coaxial with the axis with the hub and removably locked to the adapter to hold the splittable catheter coaxially about the needle during insertion of the needle and splittable catheter by an over the needle technique; and interengagement means on the adapter and the hub for cooperatively locking the axial relationship of the needle within the splittable catheter after placement of the needle within the splittable catheter so that the hub is against the second end of the adapter, the interengagement means having an unlocking member for release of the locking of the adapter and the hub.

2. The introducer of claim 1 wherein the needle has a beveled tip extending from the splittable catheter, the tip being away from the adapter with the tip of the needle beyond the splittable catheter for penetration into a lumen of a vessel when inserting the splittable catheter and needle, and wherein the needle is movable axially through the splittable catheter and the passageway during removal of the needle from the splittable catheter after insertion with an over the needle procedure and upon unlocking of the interengagement means.

3. The introducer of claim 2 wherein the splittable catheter has preferential lines of weakness which extend therealong to facilitate and direct splitting and the lines of weakness are aligned with the apex and the weakened line when the adapter and hub are fully together.

4. The introducer of claim 1 wherein the wings extend at an acute angle relative to each other and the adapter with an apex therebetween aligned parallel to the passageway therethrough and a weakened line is on a side of the adapter opposite the apex so that when the hub is removed and force applied to the wings to reduce the acute angle thereof, the weakened line and the apex will separate initiating tearing of the splittable catheter near the first end.

5. An introducer comprising:
a splittable catheter tube having an elongate tubular body with at least one preferential line of weakness positioned in alignment with an elongate dimension thereof;
an adapter with a first end and a second end and a first part on the first end and a second part on the second end, the adapter having a passageway aligned along an axis of the adapter and passing through the first part from the first end into and through the adapter to the second end, the adapter receiving and mounting to the first part of the adapter the splittable catheter tube for extending outward from the first end in alignment with the axis of the passageway and in fluid communication therewith, the first part having an expandable attachment with the splittable catheter so that the splittable catheter tears upon expansion of the first part;
a pair of wings integral to the adapter extending therefrom with an acute angle between the wings, the wings joining the adapter and defining an apex along one side of the adapter, the wings for permitting holding, handling and splitting of the adapter when the hub is removed and force applied to the wings collapses the acute angle by first breaking the adapter along a side opposite the apex and then continued collapse of the acute angle of the wings separates the adapter along the apex; and
a pair of weakened lines along the adapter with one at the apex and the other on the opposite side to encourage breaking of the adapter along the lines upon application of stress to the wings and to thereby expand the first part to tear the splittable catheter tube.

6. The introducer of claim 5 wherein the wings include a fulcrum means cooperatively associated therewith to meet during the collapse of the wings, the fulcrum means transfers the stress applied to collapse the wing to the apex.

7. The introducer of claim 6 wherein the wings have opposed facing surfaces and the fulcrum means includes ribs on the wings extending from the apex toward each other in planes normal to the facing surfaces for engagement of the ribs with one another upon collapse of the wings.

8. The introducer of claim 7 wherein the adapter is made of an inflexible polymeric substance.

9. The introducer of claim 8 wherein the adapter is a molded polymeric substance.

10. The introducer of claim 5 wherein the interengagement means is on the adapter and the hub for cooperatively locking the axial relationship of the needle within the splittable catheter tube upon placement of the needle within the splittable catheter tube so that the hub is against the second end of the adapter, the interengagement means having an unlocking member for release and unlocking of the adapter and the hub.

11. The introducer of claim 10 wherein the unlocking member extends from the hub and is movable relative thereto in response to engagement of a portion thereof with the second part upon conjugation of the needle within the splittable catheter tube and the unlocking member has a latch to connect with the second part when the hub is against the second end.

12. The inserter of claim 11 wherein the second part has a catch between the wings, the wings have opposed facing surfaces with a fulcrum means including ribs extending from the apex toward each other in planes normal to the facing surfaces for engagement of the ribs with one another upon collapse of the wings.

13. The introducer of claim 12 wherein the latch is movable from a position of nonengagement to a position of locking with the adapter upon coaxial positioning of the needle in the splittable catheter and the catch is located between the wings and is associated with the ribs.

14. The introducer of claim 13 wherein the latch has a transverse part to engage the ribs.

15. A method for using and making an introducer including the following steps:
holding with the fingers of one hand an introducer having a winged adapter with a splittable catheter and a needle and hub means having a needle and a hub in axial alignment with one another and locked to the catheter;
inserting the needle and splittable catheter with an over the needle technique into a blood vessel;
releasing the lock between the winged adapter and the needle and hub means with the finger of the one hand;
removing the needle and hub means by withdrawing the needle and hub means from the splittable catheter and adapter with the one hand; and
squeezing the wings of the adapter together to cause the adapter and the catheter to split.

16. The method of claim 15 including the additional step of:
introducing a catheter through the splittable catheter prior to squeezing the wings of the adapter together to cause the winged adapter and the splittable catheter to split.

17. The method of claim 15 including the additional step of:
attaching the splittable catheter and winged adapter by molding the winged adapter about the splittable catheter at an end thereof.

18. An introducer comprising:
an adapter with a first end and a second end and a first part on the first end and a second par ton the second end, the adapter having a passageway aligned along an axis thereof and passing therethrough to the second end, the adapter having a pair of wings extending outwardly from the adapter for use in handling, holding and splitting the adapter, the adapter having an apex parallel to the passageway and along the place where the wings attach to the adapter, the adapter with a weakened line on the side thereof across from the apex;
a splittable catheter mounted to the first part of the adapter and extending outward from the first end in alignment with the axis of the passageway and in fluid tight communication therewith, the interengagement means having a latch on the hub and a catch on the adapter, the latch movable from a position of nonengagement to a position of locking with the adapter upon coaxial positioning of the needle in the splittable catheter, the catch being located between the wings;
a needle and hub means having a needle and a hub in axial alignment with one another so the needle fits within the splittable catheter coaxial with the axis with the hub and removably locked to the adapter to hold the splittable catheter coaxially about the needle during insertion of the needle and splittable catheter by an over the needle technique; and interengagement means on the adapter and the hub for cooperatively locking the axial relationship of the needle within the splittable catheter after placement of the needle within the splittable catheter so that the hub is against the second end of the adapter, the interengagement means having an unlocking member for release of the locking of the adapter and the hub.

19. An introducer comprising:

a winged adapter with a first end and a second end and a first part on the first end and a second part on the second end, the adapter having a passageway aligned along an axis of the adapter and passing through the first part from the first end through the adapter to the second end, the adapter having a pair of laterally extending wings integral thereto extending therefrom for forming an acute angle therebetween with an apex along one side of the adapter, the pair of wings for permitting holding, handling and splitting of the adapter when the hub is removed therefrom and force applied to the wings to collapse the acute angle breaking the adapter along a side opposite the apex and continued collapse of the acute angle of the wings separates the adapter along the apex;

an elongate splittable catheter tube connected to the first part of the adapter with the passageway in fluid tight communication therewith, the splittable catheter tube having at least one line of weakness along the elongate dimension thereof, the connection between the first part and the splittable catheter tube with the adapter molded thereto to form the fluid tight communication between the adapter passageway and the splittable catheter tube;

a pair of weaken lines along the adapter with one at the apex and the other on an opposite side thereto for encouraging breaking of the adapter along the lines upon application of stress to the wings for expanding the first part to tear the splittable catheter tube;

a needle and hub means having a needle and a hub in axial alignment with one another wherein the needle fits within the splittable catheter tube coaxial with the axis with the hub removably locked to the adapter to hold the splittable catheter coaxially about the needle during insertion of the needle and splittable catheter with an over the needle technique; and interengagement means in the adapter and the hub for cooperatively locking the axial relationship of the needle within the splittable catheter upon placement of the needle within the splittable catheter so that the hub is against the second end of the adapter, the interengagement means having an unlocking member for release of the locking of the adapter and the hub.

* * * * *